(12) United States Patent
Appelt et al.

(10) Patent No.: US 7,495,435 B2
(45) Date of Patent: Feb. 24, 2009

(54) METHOD FOR THE HYPERPOLARISATION OF ATOMIC NUCLEI AND DEVICE FOR IMPLEMENTING THE METHOD

(75) Inventors: Stephan Appelt, Jülich (DE); Friedrich Wolfgang Häsing, Jülich (DE); Giovanni D'Orsaneo, Jülich (DE); Ulrich Sieling, Düren (DE)

(73) Assignee: Forschungszentrum Julich GmbH, Julich ( * ) Notice: Subject to any disclaimer, the term of this patent is extended or adjusted under 35 U.S.C. 154(b) by 0 days.

(21) Appl. No.: 10/586,000

(22) PCT Filed: Jan. 13, 2005

(86) PCT No.: PCT/DE2005/000023

§ 371 (c)(1),
(2), (4) Date: Jul. 12, 2006

(87) PCT Pub. No.: WO2005/069027

PCT Pub. Date: Jul. 28, 2005

(65) Prior Publication Data

US 2007/0080684 A1    Apr. 12, 2007

(30) Foreign Application Priority Data

Jan. 19, 2004 (DE) .................. 10 2004 002 640
May 12, 2004 (DE) .................. 10 2004 023 345

(51) Int. Cl.
*G01V 3/00* (2006.01)
(52) U.S. Cl. ...................................... 324/300; 324/305
(58) Field of Classification Search ................. 324/300, 324/312, 307, 309, 304, 305; 62/637
See application file for complete search history.

(56) References Cited

U.S. PATENT DOCUMENTS

| | | | |
|---|---|---|---|
| 5,860,295 A | 1/1999 | Cates, Jr. et al. | |
| 6,318,092 B1 | 11/2001 | Happer | 62/55.5 |
| 6,666,047 B1 * | 12/2003 | Shah et al. | 62/637 |
| 6,942,467 B2 * | 9/2005 | Deninger et al. | 417/313 |
| 2002/0107439 A1 | 8/2002 | Hersman et al. | |

FOREIGN PATENT DOCUMENTS

| | | |
|---|---|---|
| DE | 199 37 566 | 2/2001 |
| WO | WO 99/08766 | 2/1999 |

* cited by examiner

*Primary Examiner*—Louis M Arana
(74) *Attorney, Agent, or Firm*—Andrew Wilford

(57) ABSTRACT

An apparatus for hyperpolarizing atomic nuclei through optical pumping has a cylindrical optical pumping cell having an inlet and an outlet spaced therefrom. A supply of a mixture of optically pumpable species and hyperpolarizable nuclei is connected to the inlet of the cell. A nozzle at an inlet of the optical pumping cell forms and injects a jet flow of the mixture into the optical pumping cell. It is then drawn out through the outlet such that the mixture touches the inner walls of the optical pumping cell only adjacent the outlet.

19 Claims, 5 Drawing Sheets

Figure 1:
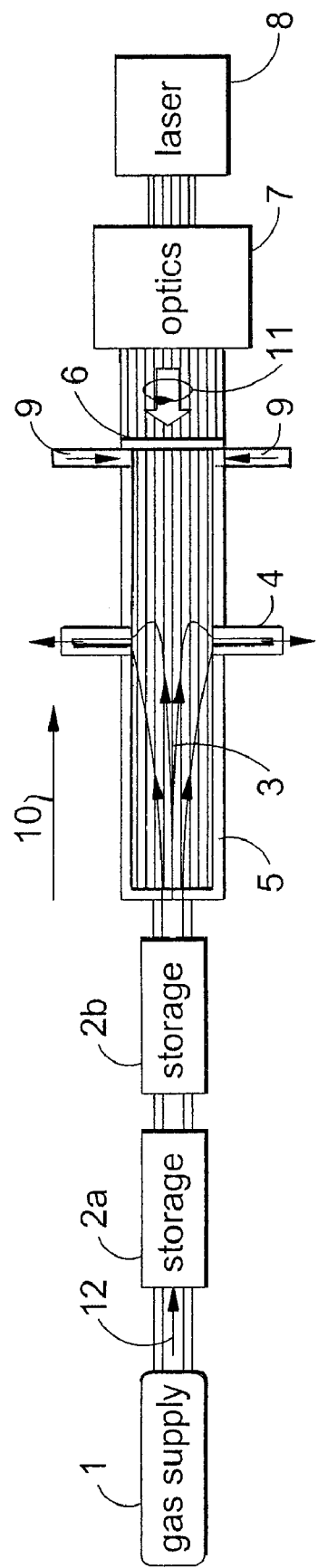

METHOD FOR THE HYPERPOLARISATION OF ATOMIC NUCLEI AND DEVICE FOR IMPLEMENTING THE METHOD

CROSS REFERENCE TO RELATED APPLICATIONS

This application is the US national phase of PCT application PCT/DE2005/000023, filed 13 Jan. 2005, published 28 Jul. 2005 as WO 2005/069027, and claiming the priority of German patent application 102004002640.8 itself filed 19 Jan. 2004 and German patent application 102004023345.4 itself filed 12 May 2004, whose entire disclosures are herewith incorporated by reference.

FIELD OF THE INVENTION

The invention relates to a method for hyperpolarizing atomic nuclei and a device for implementing the method.

BACKGROUND OF THE INVENTION

Recent developments in magnetic resonance tomography (MRT) and magnetic resonance spectroscopy (NMR) with polarized noble gases anticipate applications in medicine, physics and materials science. Polarization of noble gas nuclei may be achieved through optical pumping using alkali atoms, as described in the publication Happer, et al., Phys. Rev. A, 29, 3092 (1984).

The notion of optical pumping comprises the method developed by Kastler of significantly increasing by incident light radiation in material the occupation numbers of certain energy states relative to the state of equilibrium. By using optical pumping, the relative occupation numbers of the energy levels in atoms, ions, molecules and solid substances may be changed and ordering states induced. The occupation density of the optically pumped state differs noticeably from its thermal occupation probability according to the Boltzmann distribution. Through optical pumping of Zeeman levels, e.g parallel positioning of the magnetic moments of atoms and atomic nuclei may be obtained.

Typically, rubidium (an alkali atom) is used in practical operation in the presence of a noble gas and nitrogen making it possible to obtain a nuclear spin polarization of e.g $^{129}$Xe of about 20 percent. Such a nuclear spin polarization is about 100,000 greater than the equilibrium polarization in clinical magnet resonance tomographs at 1 T and 300 K. The drastic increase of the signal-to-noise ratio explains why new application areas in medicine, science and technology can be expected in the future.

Polarization refers to the degree of orientation (ordering) of the spins of atomic nuclei or electrons. For instance, 100 percent polarization means that all nuclei or electrons are oriented likewise. Polarization of nuclei or electrons is tied to a magnetic moment.

Polarized xenon is, for instance, inhaled by or injected in a human being. 10 to 15 seconds later, the polarized xenon accumulates in the brain. The distribution of the noble gas in the brain is determined by using magnetic resonance tomography. The result is used for further analyses.

The choice of an noble gas depends in each case on its actual application. $^{129}$Xe exhibits great chemical shift. If, for instance, xenon is adsorbed on a surface, its resonance frequency changes significantly. Moreover, xenon is soluble in lipophilic liquids. When such properties are desired, xenon is applied.

The noble gas helium is hardly soluble in liquids. The isotope $^{3}$He is therefore regularly used when cavities are concerned. The human lung is an example of such a cavity.

Some noble gases have useful properties other that those mentioned above. For instance, the isotope $^{83}$Kr, $^{21}$Ne and $^{131}$Xe have a quadrupole moment, of interest, e.g for experiments in basic research or in surface physics. However, these noble gases are very expensive, which makes them unsuitable for applications, in which greater amounts are used.

From the publication Driehuys, et al (Appl. Phys. Lett. (1996) 69, 1668) it is known how to polarize noble gases in a polarizer in the following way.

Based on a gas supply, a gas flow consisting of a mixture of $^{129}$Xe, $^{4}$He and $N_2$ is enriched in a Rb container with Rb vapor and conducted through a pump cell. Using a laser, circular polarized light is produced, i.e., light in which the spin momentum or the spin of the photons exhibits the same direction. In the pump cell, the Rb atoms are optically pumped as an optically pumpable species with the laser beam ($\lambda$~795 nm, Rb D1 line) longitudinally to a magnetic field, thereby polarizing the electron spins of the Rb atoms. The spin momentum of the photons is thus transferred to free electrons of alkali atoms. The spins of the electrons of the alkali atoms thus vary greatly from thermal equilibrium, i.e., the alkali atoms are polarized. Through the collision of an alkali atom with an noble gas atom, the polarization of the electron spins is transferred to the noble gas atom, whereby polarized noble gas forms. The polarization of the electron spins of the alkali atoms created by optical pumping of alkali atoms is thus transferred through spin exchange of the alkali electron to the nuclear spin of the noble gases, as was first shown by Bouchiat with an Rb/$^{3}$He system.

From Appelt et al (S. Appelt, A. Ben-Amar Baranga, C. J. Erickson, M. V. Romalis, A. R. Young, and W. Happer, Phys. Rev. A (1998), 58, 1412) regarding the theory of two-body collisions, it is known how to produce spin exchange between a pair of alkali-metal atoms.

From WO 99/08766 (U.S. Pat. No. 6,318,092), it is known how to apply, besides an initial optically pumpable alkali metal, an auxiliary alkali metal as a non-optically pumpable species. The optically pumpable species thereby transfers the electron-spin polarization to the non-optically pumpable species, whereby effectively an increase of the polarization degree of the noble gas occurs.

Alkali atoms are used, since they possess a large optical moment of dipole, which interacts with light. Furthermore, each alkali atom exhibits a free electron, so that unfavorable interactions between two or more electrons per atom cannot occur.

Cesium would also be a well-suitable alkali atom, which is superior when compared to rubidium for obtaining the above-mentioned effect. However, there are no lasers currently available with a sufficiently high capacity, as is needed for the polarization of xenon by using cesium.

To use a maximum possible amount of photons, when employing broad-band high-performance semiconductor lasers, optical pumping of noble gases is done at pressures of several atmospheres. Optical pumping of alkali-metal atoms thereby differs according to the type of noble gas to be polarized.

In order to polarize $^{129}$Xe, a gas mixture under a pressure of about 7 to 10 Bar is guided through a cylindrical glass cell continuously or semi-continuously. The gas mixture consists to 94 percent of $^{4}$He, to 5 percent of nitrogen and to 1 percent of xenon. The typical flow rate of the gas mixture is 1 cm per second.

In case of polarization of $^3$He, the required pressure in the polarizer is created by $^3$He itself, since the electron-spin relaxation rate of Rb-$^3$He collisions is low. For Rb—$^{129}$Xe spin exchange pumps, this is not the case, which is why the pressure is created by an additional buffer gas such as $^4$He. The various relaxation and spin-exchange rates cause various requirements of the polarizers.

For $^3$He, the nuclear-spin polarization formation times are thus on the magnitude of hours. Since, however, the rubidium-spin destruction rate for rubidium $^3$He collisions is relatively low, operation at high $^3$He pressures (>5 bar) is possible.

In contrast, for $^{129}$Xe, the nuclear-spin polarization formation times based on the greater spin-exchange effective cross section are situated between 20 and 40 seconds. Based on the very large rubidium-electron spin-relaxation rate for rubidium-xenon collisions, the xenon partial pressure should only be less than 100 mbar for optical-spin-exchange pumps in order for a sufficiently high rubidium polarization to be maintained. That is why in such polarizers $^4$He is employed as buffer gas in order to achieve line broadening.

The polarizers may be designed as flow polarizers, e.g for polarizing $^{129}$Xe or as polarizers with a sealed optical pumping cell, e.g for $^3$He.

In a flow-through flow polarizer, the gas mixture initially flows through a vessel, referred to in the following as a "supply vessel," containing a certain amount of Rb. The supply vessel with the rubidium contained therein is heated together with the adjacent glass cell to about 100 to 150 degrees Celsius. By providing these temperatures, the rubidium vaporizes. The concentration of the vaporized rubidium atoms in the gas phase is determined by the temperature in the supply vessel. The gas flow carries the vaporized rubidium atoms from the supply vessel, e.g into a cylindrical optical pumping cell. A high-performance laser in continuous operation delivering circular polarized light with a capacity of about 100 Watt penetrates by radiation the optical pumping cell axially, i.e., in the direction of flow and optically pumps the rubidium atoms in a high-polarized state. The wavelength of the laser should thereby be adjusted to the optical absorption line of the rubidium atom (Dl line).

In other words, in order to optimally transfer the polarization of light to an alkali atom, the frequency of the light must match the resonance frequency of the optical transition.

The optical pumping cell is located in a static magnetic field $B_D$ of about 10 Gauss created by coils, especially a so-called Helmholtz coil pair. The direction of the magnetic field runs parallel to the cylinder axis of the optical pumping cell or parallel to the direction of the laser beam, the magnetic field serving to guide the polarized atom. The rubidium atoms being optically highly polarized due to the light of the laser collide in the glass cell with the xenon atoms, among others, and release their polarization to the xenon-atoms.

At the exit of the optical pumping cell, rubidium deposits on the wall due to the high melting point compared to the melting points of the other gases. The polarized xenon or the residual gas mixture is passed along from the optical pumping cell and into a freezing unit consisting of a glass flask, whose end is submerged in liquid nitrogen. The glass flask is furthermore located in a magnetic field with a strength exceeding 1000 gauss. The highly polarized xenon gas deposits on the inner glass wall of the freezing unit as ice.

At the outlet of the cooling unit, the remaining gas ($^4$He and $N_2$) is generally guided via a needle valve and finally released. The flow rate of the whole device may be controlled via the needle valve and a with measuring device.

If the flow rate increases too much, then there is no time for transferring the polarization from the rubidium atoms to the xenon atoms. Thus only minor polarization is obtained. If the flow rate is too low, then too much time will lapse before the desired amount of highly polarized xenon is frozen. Due to relaxation in the Xe ice, the polarization of the xenon atoms hence decreases. The relaxation of the xenon atoms is greatly delayed due the freezing, and also a strong magnetic field, which the cooling unit is exposed to. That is why it is necessary, following polarization, to freeze the noble gas xenon as quickly as possible and without loss. Relaxation through freezing cannot be entirely avoided, However, at 77 K, one to two hours remain before the xenon polarization has decreased enough so that further application of the initially highly polarized gas no longer is possible.

A polarizer of the above-mentioned type always exhibits junctions. Junctions occur where at least two lines, through which polarized gas is guided, are connected with one another, whereby the lines usually consist of glass. The connection is established by a connecting element, such as flanges.

To polarize a single free alkali atom requires a certain energy. The required energy equals the resonance frequency for increasing the free electron of the alkali atom from a ground state to an excited state. In order to transfer the energy from a laser to the alkali atom in an optimal fashion, the frequency of the laser light should be adjusted to the resonance frequency of the alkali atom. Some lasers emit their light within a certain frequency spectrum. We are therefore not concerned with a single frequency, but a distribution of frequencies. The available laser spectrum is characterized by the so-called line width. In order to polarize alkali atoms commercially, broad-band semiconductor lasers are provided, whose frequency and line width are adjusted to the resonance frequency or the optical line width of the alkali atom.

In order to better transfer the energy from a laser to alkali atoms, collision partners for the alkali atoms are provided during polarization. As collision partners serve especially the $^4$He atoms. Due to the interaction or collisions with the helium atoms, the optical line width of an alkali atoms expands. Increasing the width of this atomic spectrum makes it possible to use spectrally wide and therefore economical lasers.

The number of collisions between an alkali atom and a collision partner such as *He increases with increasing pressure. For $^4$He, for example, the expansion of the optical line width of the alkali atom is proportional to the pressure of the helium gas. In addition, *He has the value characteristic of only affecting slightly the polarization of the alkali atoms. For the polarization of $^{129}$Xe, a gas mixture consisting to 94 Percent of $^4$He and with a pressure of about 10 bar is usually employed.

The laser known from prior art with a power of 100 Watt for the hyperpolarization of the Rb electrons concerns a glass-fiber-coupled diode laser with a typical spectral width of 2 to 4 nanometers. With a gas pressure of 10 bar, the line width of the optical transition of rubidium atoms is expanded to about 0.3 nanometers. In the present rubidium-xenon polarizers, in which high-performance diode lasers with a typically 2-nanometer line width are applied for optical pumping, only a fraction of the laser light is therefore utilized.

The partial pressures of $^4$He are up to 10 bar in the gas mixture. This is very high compared with the other partial pressures (xenon or nitrogen), and is to ensure that polarized alkali metal or noble-gas atoms rarely reach the inner wall of the glass cell and lose their polarization there, e.g through interaction with paramagnetic centers. With increasing partial pressure of $^4$He, the probability that the polarized atoms collide disadvantageously with the inner wall of the cell decreases.

A polarized alkali atom, such as rubidium, is able to produce fluorescence radiation. If such radiation is captured by a further polarized alkali atom, depolarization of the alkali atom occurs. The nitrogen applied for the polarization of noble gases in the gas mixture serves to capture the fluorescence radiation in order to reduce the above-mentioned undesired depolarization. The nitrogen element in the gas mixture exhibits only a small partial pressure, as does similarly xenon. This partial pressure is typically about 0.1 bar.

The heavy noble-gas atoms, e.g xenon atoms, cause strong relaxation of the polarization of the alkali atoms when colliding with the alkali atoms. In order to maintain the polarization of the alkali atoms as high as possible during optical pumping, the partial pressure of the xenon gas in the gas mixture must be correspondingly small. Even with a xenon partial pressure in the gas mixture of 0.1 bar, laser capacities of around 100 Watt are required in order to obtain a polarization of the alkali atoms of about 70 percent in the whole test volume.

In prior art, optical pumping cells of glass blown from one piece are employed. This means that the windows, through which the laser light enters and exits, is always curved or rounded. During entry and exit of the laser light, undesirable and disadvantageous lens effects occur. The laser light is focused or widened, whereby the degree of polarization deteriorates considerably. The effective cross section of the optical pumping cell is therefore not uniformly illuminated by the laser light.

A gas volume with suitable composition is compressed according to prior art by a cylindrical optical pumping cell. The laser light producing the polarization is absorbed in the optical pumping cell. The pump beam thereby radiates through the optical pumping cell in the direction of flow of the mixture comprising the optically pumpable species and the atomic nucleus to be hyperpolarized parallel to the magnetic field.

U.S. patent 2002/0,107,439 A1 discloses how laser light is radiated into a optical pumping cell against the current of a flowing mixture.

As a disadvantage, all previously known prior-art methods and devices for hyperpolarization provide only a comparatively low degree of polarization of the nuclear spins, at a maximum about 40%. The reason for this is interactions in the form of collisions of the alkali metal or noble gas against the inner walls of the optical pumping cell.

OBJECTS OF THE INVENTION

The object of the invention is therefore to make available a method for hyperpolarizing atomic nuclei and especially noble gas nuclei, which results in an increase of the degree of polarization.

A further object of the invention is to make available a device for implementing the method.

SUMMARY OF THE INVENTION

The method according to the invention provides for the transfer of a polarization created by a laser of an electron spin of an optically pumpable species in a mixture onto the nuclear spin of an atom to be hyperpolarized. The mixture comprises the optically pumpable species, the nuclei to be polarized and possibly further components, such as buffer and quench gases, as well as possibly a further alkali metal type as an auxiliary alkali metal.

The components of the mixture or other inert components for hyperpolarization are fed by means of a suitable design of the inlet of the optical pumping cell for these components in such a way that the optically pumpable species and/or nuclei to be hyperpolarized do not come in contact with the inner walls of the optical pumping cell, or only slightly. This prevents unfavorable interactions in the form of collisions of the alkali metals and/or the noble gas against the inner walls of the optical pumping cell, which otherwise would reduce polarization of the electrons of the optically pumpable species and the nuclei to be hyperpolarized along the effective cross section of the optical pumping cell.

As an advantage, it is possible for the hyperpolarization of inert compounds, to feed buffer gases to the optical pumping cell in such a way that the relaxation of the optically pumpable species and that of the atomic nuclei to be hyperpolarized is avoided through collisions at the inner wall.

The mixture with optically pumpable species and nuclei to be hyperpolarized may, however, also itself be fed as a jet flow cell into a optical pumping cell. The jet flow cell comprises the mixture. Its components do not touch the inner walls of the optical pumping cell due to its embodiment in the form of a jet flow cell. This measure alone causes the optically pumpable species and/or the nuclei to be hyperpolarized not to touch the inner walls of the optical pumping cell.

Depending on the gas pressure and the flow rate of the mixture, the jet flow cell and/or the bypass flow is formed and fed into the optical pumping cell in such a way that the lingering period of the hyperpolarized optically pumpable species and that of the hyperpolarized nuclei in the optical pumping cell is lower than the time for their diffusion up to the inner walls of the optical pumping cell.

The formation of the bypass flow and/or jet flow cell thus entails that the mixture with the hyperpolarized optically pumpable species and the hyperpolarized nuclei can only touch the inner walls at the position at which the mixture is guided out again from the optical pumping cell for the purpose of enrichment.

Relaxation of the optically pumpable species and/or the hyperpolarized nuclei due to collisions at the inner walls of the optical pumping cell is thus complete obviated.

The jet flow cell may be formed as a thin layer with a thickness of e.g 1 cm and/or possibly less than 1 cm diameter.

The mixture will then be injected as a jet flow cell in the optical pumping cell and does not touch its inner walls, or only to a much lesser extent as is the case according to prior art by simply pressing the mixture through a optical pumping cell. No convection currents appear at the inner walls. The flow rate of a volume element is, e.g about 0.5 cm per second and the pressure in the optical pumping cell, e.g 7-15 bar.

In addition, the device according to the invention features means for injecting the mixture into the optical pumping cell as a jet flow cell, so that the mixture will not collide with the walls, whereby wall relaxation is avoided. Such a flow polarizer will be referred to as a jet polarizer in the following.

A nozzle may be provided as a means for forming the jet flow cell. The nozzle is connected with the gas supply of the optical pumping cell and exhibits dimensions capable of forming a jet flow cell of the mixture. Moreover, the gas mixture is injected with an appropriate pressure via the nozzle in the optical pumping cell.

An especially simple and effective optical pumping cell with reduced wall relaxation relative to prior art provides for inclining the inlet and/or outlet connection(s) with a defined angle, rather than using a 90° angle (relative to the longitudinal axis of the cell).

A gas supply comprises the lines and the storage tanks for a certain species, such as the optically pumpable species and other inert components, as well as for the nuclei to be hyperpolarized. Several gas supplies deliver the various gases that are needed for the hyperpolarization of a certain type of nuclei or noble gases. Mixing chambers for mixing the various components may be provided.

The components of the jet flow cell injected in the optical pumping cell through the nozzle do not touch the walls, so that a wall relaxation of the optically pumpable species and the hyperpolarized nuclei is avoided. In effect, the formation of the jet flow cell by the device according to the invention causes a rise in the degree of polarization, when implementing the methods.

The method is, moreover, implemented such that the distance between the end of the jet flow cell, at which the mixture is guided out of the optical pumping cell, and the laser-light inlet window(s) is chosen sufficiently large so that the components of the mixture, especially the optically pumpable species cannot settle on the inner walls of the laser-light inlet window(s).

This measure, in itself, also causes a clear increase of the polarization of the hyperpolarized atom nuclei.

The laser-light inlet window of the optical pumping cell may in addition exhibit a maximum distance to the inlet of the optical pumping cell for the optically pumpable species.

The thickness of the optically pumpable species may thus be chosen very large, e.g at least $10^{14}$ cm$^{-3}$ $^{85}$Rb atoms and above, without causing the so-called unfavorable effects of the optically pumpable species settling at the laser-light inlet window(s).

Within the scope of the invention, it was realized that for prior-art polarizers with in- and outlets for the mixture at a right angle to one side wall of the cylindrical optical pumping cell, a thin layer of the optically pumpable species settles over time at the inner surface of the laser-light inlet window due to the spatial proximity to the inlet for the mixture, which layer when exposed to a pump beam with high power intensity evaporates while a boundary layer <0,3 mm) of great thickness forms. Since the atoms in this boundary layer are almost non-polarized, a large proportion of the performance of the pump beam is absorbed in this boundary layer (>50%). This performance absorbed in the boundary layer is no longer available for the actual pumping process in the cell. Moreover, the strong temperature gradient according to prior art appearing between this boundary layer and the other cell volume stimulates convective currents in the cell. This causes the transport of the gas at the cell walls to accelerate and wall relaxation to increase further. Moreover, wall relaxation of the nuclear spins is increased dramatically due to the contact with the boundary layer. The flow of the mixture according to prior art thus occurs in a U-shaped fashion.

The method according to the invention may also be implemented such that the bypass flow consisting of an inert compound is guided into the optical pumping cell in order to separate the mixture from the inner walls.

The inlet window(s) for the laser(s) is/are rinsed with a bypass flow. The bypass flow is guided into the optical pumping cell such that it encloses the jet flow cell and rinses the inner walls of the optical pumping cell. The bypass flow has no adverse effects relative to the hyperpolarization.

The bypass flow comprises advantageously an inert compound, which is needed for the hyperpolarization of a certain nucleus. As an example, a bypass flow consisting of $^4$He for the hyperpolarization of $^{129}$Xe may be mentioned.

The bypass flow is created by means comprising, e.g a nozzle and at least one separate gas supply connected therewith, with which a thin bypass flow for rinsing the inner walls of the optical pumping cell is created and guided thereinto. This will cause the mixture in the jet flow cell not to collide with the walls. Wall relaxation of the optically pumpable species and the nuclei is thus prevented.

The laser may, especially in case of a cylindrical optical pumping cell, be arranged such that the laser light in a counter current, i.e., antiparallel to the direction of flow of the mixture flowing in the optical pumping cell and the magnetic field, will produce a further increase of the degree of polarization of the nuclear spins of the mixture exiting the cell versus a flow polarizer with a direction of radiation of the laser lights with or against the direction of flow the mixture.

In a further especially advantageous embodiment of the invention, the walls of the optical pumping cell are cooled during the process. Moreover, the device may comprise, e.g a thermo box. A device comprising means for cooling the walls differ from the previous devices, such as flow polarizers, in which the walls always are heated at the same time. This is possible due to separate heating for the components of the mixture before the inlet of the optical pumping cell and the formed jet flow cell, since the latter causes prevention of wall contact of the optically pumped gases during transit time.

This measure advantageously optimizes heat removal from the gas mixture. A further especial advantage is that non-polarized atoms such as alkali metals are not released from the inner walls.

In a further embodiment of the invention, the spin exchange during the process is transferred indirectly to the nuclear spin of a nucleus to be hyperpolarized. The spin exchange is thereby initially transferred from the electrons of an optically pumpable species to the electrons of at least one species that is not optically pumpable by the laser(s) and from there transferred to the nuclei of the nuclei to be hyperpolarized. The laser light does not pump the non-optically pumpable species. Then, a greater thickness of the non-optically pumpable species versus the optically pumpable species is advantageously selected. A further advantageous result is that non-optically pumpable species exhibiting a high efficiency, especially an efficiency close to 1, may be selected for the transfer of the electron spin polarization to the nuclear spin.

The hyperpolarization device comprises for this purpose at least two storage containers for the optically pumpable species and the non-optically pumpable species, whereby these are also used for indirect spin-exchange optical pumping. The storage containers are each advantageously arranged in a separate gas supply for the device and provided with their own heating.

The device is furthermore designed such that the laser-light inlet window of the optical pumping cell exhibits a maximum distance to the inlet of the optical pumping cell for the optically pumpable species. The advantageous result is that the optically pumpable species will not settle at the inlet window.

The laser-light inlet window of the optical pumping cell may especially advantageously exhibit a distance to the exit of the optical pumping cell for the mixture that is large enough to prevent settling of the optically pumpable species on the inner wall of the laser-light inlet windows. Through suction ducts and lines, the mixture is sucked off radially to the optical pumping cell. We are thus concerned with a flow-through polarizer.

The formation of a bypass flows, a jet flow cell, the above-mentioned minimum distances of the mixture from the inner walls depending on flow rate and pressure, as well as appropriate laser devices, each on their own result in the avoidance of interaction of the mixture with the inner walls of the optical pumping cell and an increase in the degree of polarization during the process. In combination with one another, a further increase of the degree of polarization of the nuclei to be polarization may be obtained.

The coils for creating a magnetic field are arranged such that the direction of the magnetic field is against or in the direction of the laser beam.

As optically pumpable and possibly non-optically pumpable species, especially alkali metals are selected, since they exhibit a great moment of dipole.

The method according to the invention is especially suited, e.g for hyperpolarizing $^{129}Xe$ by using $^{85}Rb$ alone, or by using $^{a5}Rb$ as an optically pumpable and a cesium isotope as non-optically pumpable species. However, it may also be hyperpolarized using $^{85}Rb$ and/or the cesium isotope, or even $^{13}CO_2$.

The mixture is guided through the flow-through polarizer, either continuously or semi-continuously. In case of $^3He$, a polarizer with closed optical pumping cell is used.

The invention will be described below in reference to examples and attached drawings.

BRIEF DESCRIPTIONS OF THE DRAWINGS

FIG. 1 shows a device according to the invention for forming a free beam, which is designed in a simple and compact manner.

The injection (beam) polarizer in FIG. 1 is provided with a single gas supply 1. The gas supply 1 ensures the delivery of all gases needed for hyperpolarization. Based on gas supply 1, the gas gas mixture 12, represented by the bold-faced arrow, flows successively through two storage containers 2a, b (intended) for two different alkali types. The first storage container 2a contains an alkali metal as optically pumpable species, the second storage container 2b contains a non-optically pumpable species or vice versa. A laser 8 with polarization optics 7 is arranged such that the laser light 11 enters the test cell 5 against the direction of flow of the free beam 3 through the inlet window 6.

The device is suitable for indirect spin exchange optical pumping e.g., with an optically pumpable alkali metal and a non-optically pumpable alkali metal.

According to FIG. 1, the gas mixture 12 is enriched with, e.g., $N_2$, $^4He$ and $^{129}Xe$ in the storage container 2a, b with alkali vapors, and expands via a circular nozzle with a diameter of 1 cm (not shown) in the form of a free beam 3 into the test cell 5. The free beam is dimensioned such that the components of the gas mixture at a preset pressure of the gas mixture of about 5 to 10 bar do not touch the inner walls of the test cell 5 during flow-through time of the free beam. This will prevent wall relaxation of the optically pumpable species and the hyperpolarized atom nuclei.

The gas mixture 12 in the free beam 3 is radially sucked off with a total of six suction ducts 4, advantageously preventing it from laser-light 11 inlet window 6 and settling of the optically pumpable species there. The hyperpolarized nuclei are thus enriched.

The optical pumping beam 11 is radiated here against the flow, i.e., antiparallel to the direction of flow of the free beam 3, and longitudinally to a magnetic field 10 into the test cell 5.

Optionally, in order to avoid settling of alkali metals on the pump-beam inlet window 6, the inlet window 6 may be rinsed with a bypass flow 9 consisting of an inert gas, e.g., $^4He$.

For this, additional inlets for the bypass flow 9 are arranged near the inlet window 6. The design according to FIG. 1 is especially compact.

The laser 8 and the polarization optics 7, however, may also be arranged such that the pump beam radiates through the free beam 3 perpendicularly to the direction of flow of the free beam 3. This design is not as compact as the one according to FIG. 1, however, it advantageously ensures that the free beam 3 exhibits homogenous alkali-metal polarization over its entire volume, especially when the free beam 3 is dimensioned with a height of only a few millimeters and/or thickness.

The free beam may equally well be designed with only one optically pumpable species and the nuclei to be hyperpolarized. In this case, a device without a storage container for a non-optically pumpable species is needed.

Figure 2:
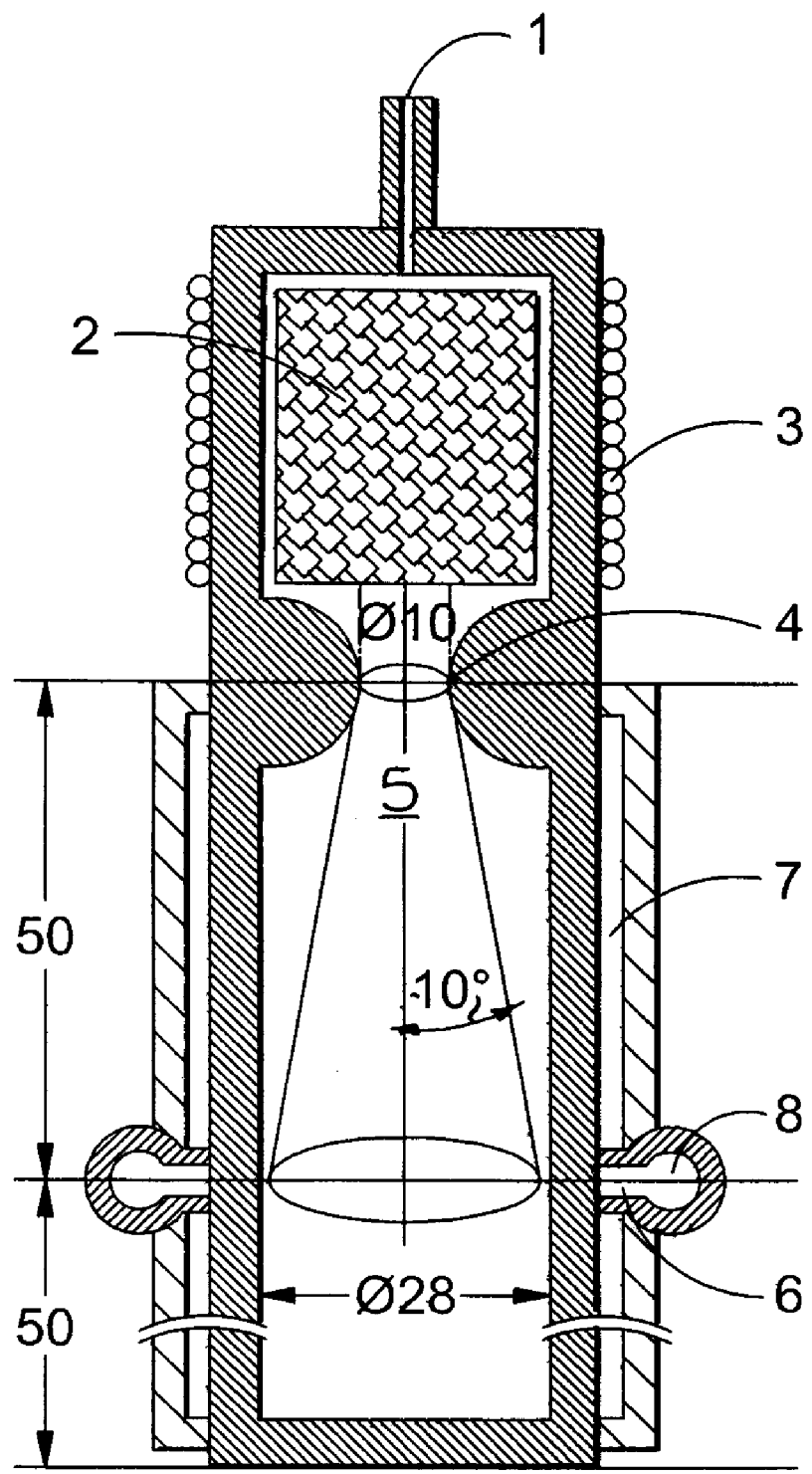

FIG. 2 shows such a device for the formation of a free beam 5, resulting in an increased degree of polarization due to the avoidance of wall relaxation, whereby only one optically pumpable species are guided into the test cell besides the other components. The diameter indications are provided in millimeters. The gas pressure in the cell is about 7 to 15 bar.

Figure 3:
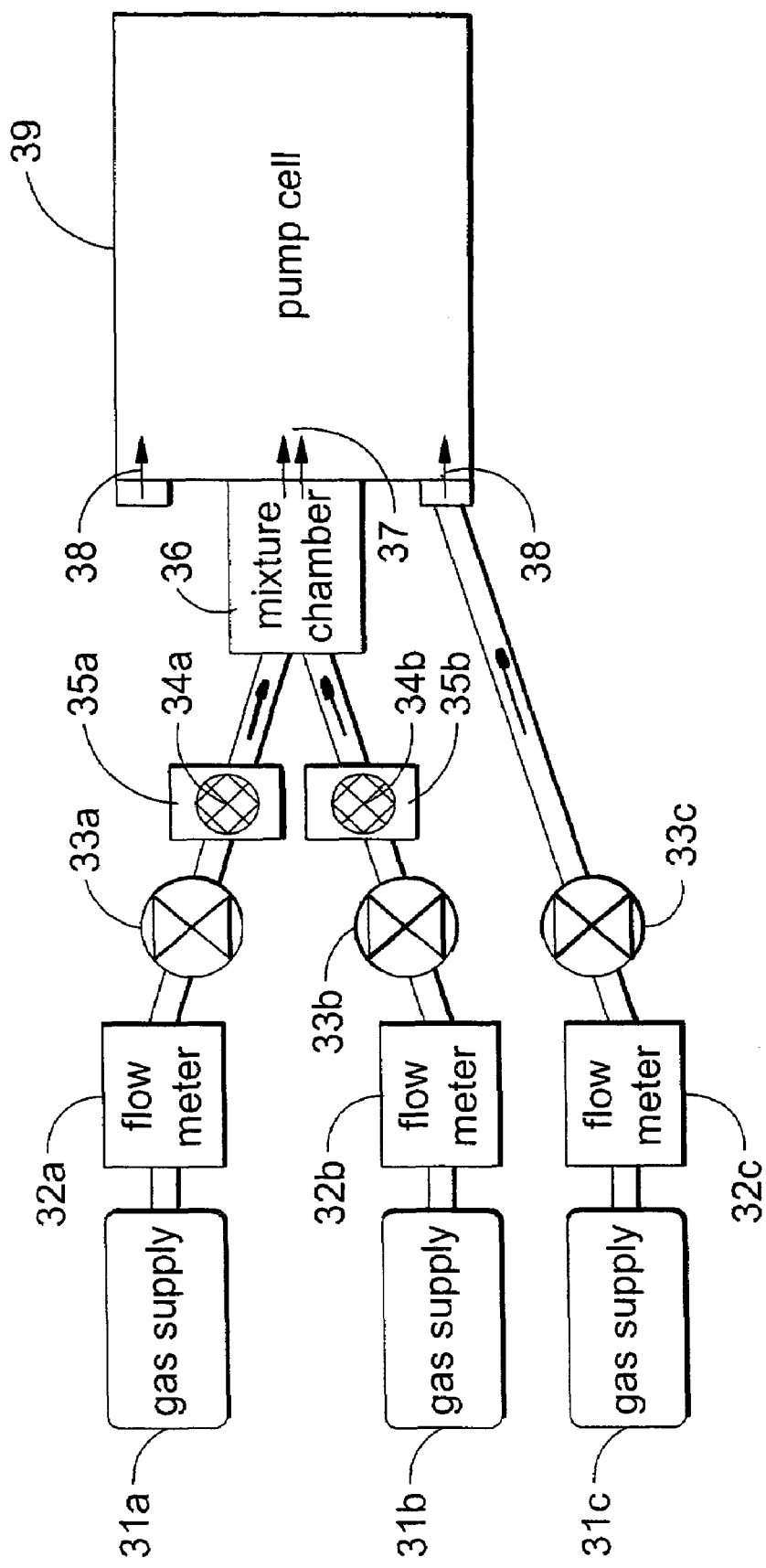

FIG. 2 shows, moreover:
 1. Gas supply
 2. With a porous metal body or metal plating (Cu, Pt, etc.) vapor-deposited with alkali
 3. Heating (micro-wave, light, hot air)
 4. Nozzle
 5. free beam
 6. Suction ducts for the free beam
 7. Gas or water cooling
 8. Collecting flue for polarized gas FIG. 3 is a schematic depiction of a device with two storage containers 34a and 34b for an optically pumpable species, e.g., $^{85}Rb$ and a non-optically pumpable species, e.g., cesium. This device is also suitable for indirect spin exchange optical pumping e.g., with an optically pumpable alkali metal and a non-optically pumpable alkali metal.

Based on the mutually independent gas supplies 31a and 31b, a gas flow, e.g., of $N_2$, $^4He$ and $^{129}Xe$, is controlled by the flow meters 32a and 32b, as well as needle valves 33a and 33b, independent of one another, and fed to the storage containers 34a and 34b.

The alkali vapor gases are enriched in the storage containers. Each storage container features its own heating 35a and 35b. Depending on the choice of optical pumpable species in storage container 34a, and the non-optically pumpable species in storage container 34b, the volume gas flows are thereby conducted in a controlled fashion to the mixture chamber 36.

The heating systems 35a and 35b arranged independently of one another advantageously make it possible to set different vapor pressure densities and temperatures for the optical pumpable species A1 and the non-optically pumpable species A2. This results in further optimization of the method.

In Mixing chamber 36, the gases are mixed with one another and from there expanded into pump cell 39, the optically pumpable species A1 and the non-optically pumpable species A2 thus only contact one another in mixing chamber 36. From mixing chamber 36, the gas mixture 37 reaches pump cell 39, in which the atom nuclei are hyperpolarized due to indirect spin exchange optical pumping. The device serves to better control the mixture ratios of the mixing ratios of the alkali types.

FIG. 3 shows the creation of a $^4He$ bypass flow 38, with which only the effect according to the invention is obtained, i.e., achieving hyperpolarization without wall contact of the optically pumpable species and/or hyperpolarized atom nuclei. The bypass flow 38 ensures improved heat removal and an alkali-free atmosphere at the inner walls of the test cell 39, however, the gas mixture 37 may, of course, also be implemented additionally as a free beam. In order to form the bypass flow 38, an individual gas supply 31c, as well as a flow meter 32c and a needle valve 33c, are provided. Two inlets at the upper and lower part of the test cell 39 are shown, whereby only the lower one connected with the gas supply is depicted for reasons of space. Naturally, the upper inlet 38 is likewise connected with a separate gas supply. In case the laser is arranged according to the reverse flow principle, the bypass flow may also be guided in the test cell such that the laser inlet window is rinsed with the bypass flow.

FIG. 3, however, does not show the laser device, or the polarizer outlet for the gas mixture.

Figure 4:
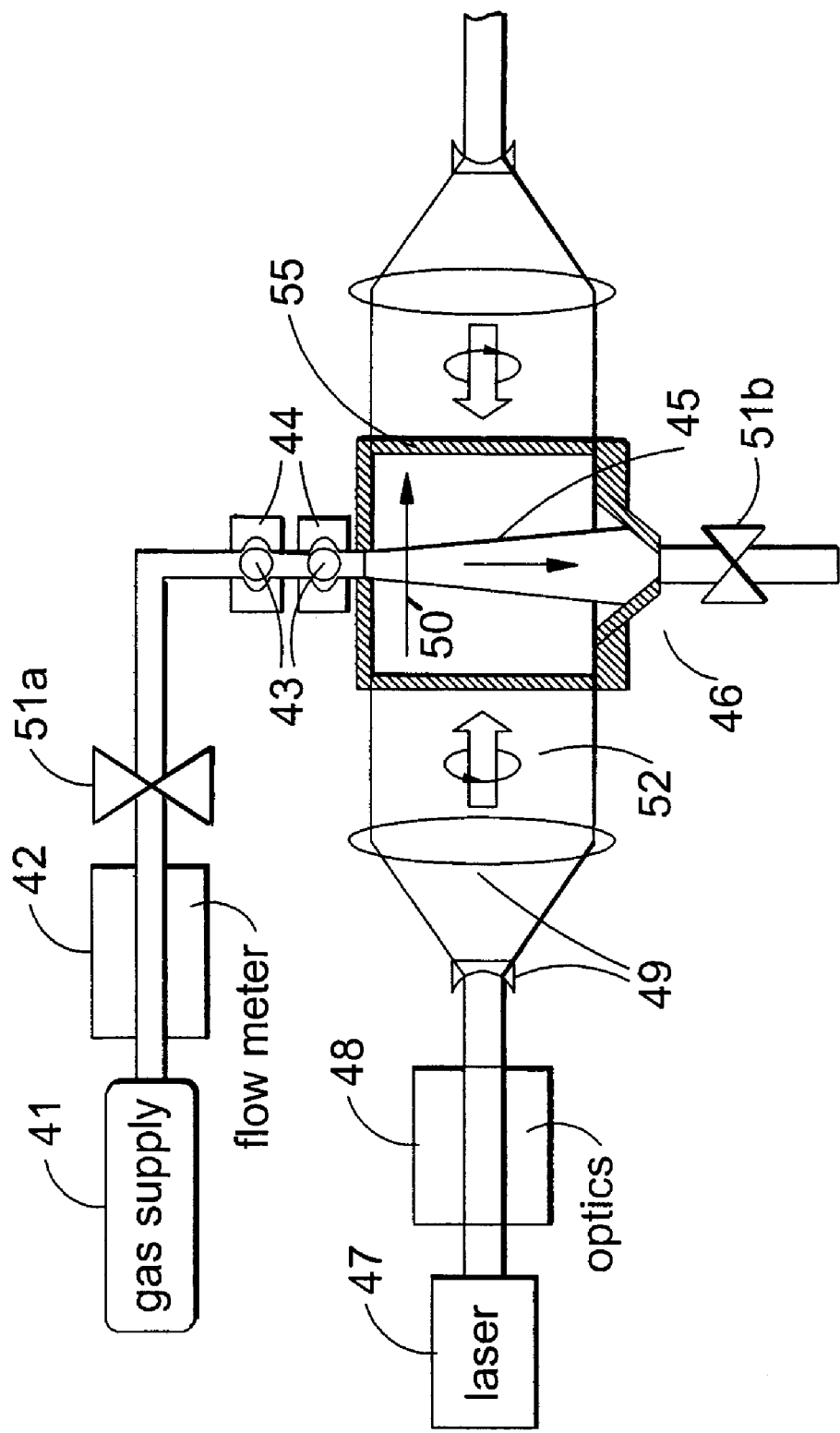

FIG. 4 is a schematic representation of a device, with which two types of alkali species A1 and A2 are guided in a controlled manner in a test cell 55, whereby wall relaxation is completely prevented due to the inplemented free beam 45.

The device is suitable for indirect spin exchange optical pumping, or also simple indirect spin exchange optical pumping, as is the device in FIG. 1. In the latter case, the non-optically pumpable species manages without a container 43 and heating 44.

A gas mixture consisting of, e.g., $^{129}Xe$, $^{4}He$ and $N_2$, is conducted from a gas supply 41 via the flow meter 42 and the needle valve 51a into both storage container 43, and there enriched with the alkali vapors A1 and A2. The ratio of the concentrations of both alkali species is controlled by separate heating [devices] 44, e.g., FF heating of the storage container 43. $^{85}Rb$ may be chosen as optically pumpable species and a cesium isotope as non-optically pumpable species. The volume flow is controlled by the needle valves 51a, 51b at the in- and outlet of the test cell 55. The flow meter 42 is arranged for this purpose before the storage containers 43, 44. Each storage container 43, 44 may also be provided with their own gas supplies and valves.

The gas mixture enriched with alkali atoms flows into the test cell 55 through a nozzle at its inlet and there forms a free beam 45 due to the dimensions of the nozzle, which may be designed as the one shown in FIG. 2.

The laminar free beam 45 is completely penetrated by radiation from the two lasers arranged perpendicularly to the direction of flow of the free beam 45 completely and thus with an extremely high pumping performance. The figure shows only the left-hand laser 47 together with its polarization optics 48 and the telescope with cylinder lenses 49 for reasons of space, whereas of the right-hand laser, only the telescope with the cylinder lens is shown without a reference mark. The circularly polarized laser light 52 enters also through both vertical inlet windows into the test cell 55 and radiates completely through the free beam 45.

The free beam 45 is formed as a thin layer with a height of about 20 mm, and a thickness of about 1 mm at the inlet of test cell 55, and a height of about 32 mm and a thickness of about 13 mm at the exit 46 of test cell 55. This will advantageously allows for the thickness [or: density] of the optically pumped alkali species to be high, since both perpendicularly arranged lasers only need to penetrate a layer of about 1 cm in diameter. A further advantage is that due to the low layer thickness of the free beam 45, absorption of fluorescence radiation is reduced. Moreover, opposite [or: in contrast to] a cylinder-symmetrical beam of the mixture, increased relaxation of the $N_2$ molecules used for quenching the excited alkali atoms occurs due to increased heat removal through the large boundary surface [or: interface] between the free beam 45 and the surrounding gas.

The risk that the vertical laser-beam inlet window will be covered by alkali metals is low, if sufficient distance is kept between the free beam 45 and the vertical laser-light inlet windows. The current of the free beam 45 advantageously no longer needs to be diverted when flowing out of test cell 55.

A further advantage of spin exchange optical pumping using a free-beam arrangement is that the whole test cell 55, as shown in FIG. 2, need not be heated. Only the amount of heat needed for vaporizing the alkali metal(s) and heating the gas flow is supplied. That is why, this heat needs to be removed to the environment. This allows for a significantly more compact design versus the previously known devices.

A magnetic field 50 is likewise aligned perpendicularly to the free beam 45 by arranging one or more coils.

The free beam 45 may be gnided through two (not shown) shields arranged perpendicularly to the free beam 45 near the exit 46 in order to avoid reflux to the exit side of the polarizer.

The free beam 45 may be guided for the purpose of enrichment behind the valve 51b at the exit side of the cell 55 into a cool solvent with great solubility for the hyperpolarized gas in cell 55.

The molecules in the free beam 45 have no wall contact during the whole polarization process in test cell 55.

FIG. 4 represents a device, in which the optical axis of the pump beam 52 and the magnetic field 50 is perpendicular to the direction of flow of the free beam 45. For the reasons described, this represents the optimal solution for perfect spin exchange optical pumping. However, the configurations shown in the previous figures, in which the significant advantages of contactless pumping are retained, while allowing for simpler and more compact implementation, are also possible.

The devices depicted in FIGS. 1 to 4, and the free beam method may be designed without limiting the invention also for simple optical pumping, i.e., used without indirect spin exchange pumping. In this case, only devices with one single storage container for an optically pumnpable species are needed. All devices may be provided with thermo boxes for the test cell. It is possible without limiting the invention in any way to provide the above-mentioned devices with means for forming a bypass flow.

The above-mentioned indirect spin exchange optical pumping may be described for any given systems like this:

$$P_{A1}(z) = s_z \cdot \frac{R(z)}{R(z) + \gamma_{sd}^{A1}} \quad (1)$$

$$P_{A2}(z) = P_{A1}(z) \cdot \frac{\gamma_{ex}^{A2,A1}}{\gamma_{ex}^{A2-A1} + \gamma_{sd}^{A2}} \quad (2)$$

$$\gamma_{ex}^{A2,A1} \cong \langle \sigma_{A2,A1} \cdot v \rangle \cdot [A1] \quad (3)$$

where $P_{A1}$ (z) is the volume-mediated degree of polarization of the optically pumnpable (alkali) species A1, $\gamma^{A1}{}_{sd}$ is the electron spin relaxation rate for the optically pumpable species A1, $P_{A1}$ (z) is volume-mediated degree of polarization of the electron of the non-optically pumpable (alkali) species A2, $S_z$ is the photon spin R(z) is the optical pump rate per alkali metal atom at the z position $\gamma^{A2,A1}_{ex}$ is the spin exchange rate for optically pumpable species A1 on non-optical pumpable species A2, and $\gamma^{A2}_{sd}$ is the electron spin relaxation rate for the non-optical $$P_{EG}(z) \sim P_{A2}(z) \cdot \frac{\gamma^{EG,A2}_{se}}{\gamma^{EG,A2}_{se} + \gamma_W} \quad (4)$$

$$\gamma^{A2}_{se} = \langle \sigma_{EG,A2} \cdot v \rangle \cdot [A2] \quad (5)$$

where $P_{EG}$ is volume-mediated degree of polarization of the nuclei (noble gas) to be hyperpolarized, $\gamma^{A2}_{sc}$ is the spin exchange rate of non-optically pumpable species A2 on the nuclear spin EG, $\gamma^W$ is the wall relaxation rate of the nuclear spins, 30

σEG,A2 is the effective cross section for the non-optically pumpable species A2 and the nucleus EG to be hyperpolarized, σEG,A2 $^V$ is the average value of the of the effective cross section over the relative velocity v.

The index „ex" for exchange refers to the spin exchange between optically pumpable A1 species and non-optically pumpable species A2. The index "se for spin exchange refers to the spin exchange between non-optically pumpable species A2 and the atomic nucleus Ed.

The generally indicated equations for indirect spin exchange optical pumping show that on condition that the electron spin relaxation rate of the optically pumpable species $\gamma^{A1}_{sd}$ is kept lower than the laser pump rate R, a hyperpolarization effect of atomic nucleus produced, provided the electron spin radiation rates $\gamma^{A1}_{sd}$ and $\gamma^{sd}$ are less than the spin exchange rate $\gamma^{A2,A1}_{ex}$ between optically pumpable species A1 and non-optically pumpable species A2.

Since the spin exchange between the optically pumpable species A1, and the non-optically pumpable species A2, and possibly further species is spin-maintaining, and has a large effective cross section, spin polarization of the alkali metal species A1, which is optically pumped, may effectively be transferred to the atoms of species A2, which are non-optically pumped. This also applies, when the thickness of A1 is R =10$^6$ s$^{-1}$. The electron spin relaxation rate $\gamma^{ab}_{sb}$ of rubidium as optically pumpable species A1 is at a $^{129}$Xe partial pressure of 0,1 bar about 3*10$^4$ s$^{-1}$.

To illuminate the pump cell optimally, as the density of rubidium is sufficient small, i.e., the density of the optically pumped alkali species A1 is chosen such that the [a] alkali-metal species A2 is higher than the density of the A1 species.

The notion of effective cross section is a measure of the probability for interaction of the different particles and the occurrence of nuclear spin polarization of the noble gas. It is defined as a quotient of the number of processes that occur during a certain time period over the number of particles that enter per unit of area during this period in the reaction area.

The equations apply to any systems. The equations therefore describe both the hyperpolarization of noble gas nuclei with two species of alkali metals, as well as the hyperpolarization of $^6$Li, $^{13}$C and other nuclei by means of suitable optically pumpable and non-optically pumpable species.

The gas throughput and thus the production amount of the nuclei to be hyperpolarized may be increased.

For instance, for the rubidium-cesium-xenon system, the following calculation may be formulated:

The density of rubidium atoms as optically pumpable species A1 in the pump cell is 10$^{14}$ cm$^{-3}$. The laser performance is R =10$^6$ e$^{-1}$. The electron spin relaxation rate $\gamma^{rb}_{sd}$ of rubidium as optically pumpable species A1 at a partial pressure of $^{129}$Xe of 0.1 bar is about 3*10$^4$ s$^{-1}$.

The laser illuminates the pump cell optimally, since the density of rubidium is sufficiently low. This means that the density of the optically pumped alkali species A1 is chosen such that the optical pump beam penetrates with sufficient depth in the pump medium.

The electron spin of the rubidium atom is polarized, see equation (1). Due to the relatively low density of the rubidium atom, the volume-mediated degree of polarization <$P_{RB}$> (z) is maximal, i.e., a value of 90% is produced therefor, since the photon spin polarization $s_z$ exhibits a value of about 97%.

In order to increase the degree of polarization of $^{129}$Xe, a maximum degree of polarization of rubidium as optically pumpable species is thus a requirement, whereby the laser pumping rate is kept greater than the electron spin relaxation rate of the optically pumpable species (here: R(z) >$\gamma^{Rb}_{sd}$). If the rubidium density $n_{rb}$ in the pump cell is too high, as in the indicated example, then the degree of polarization of rubidium declines rapidly with the position z.

With rubidium densities above 10$^{14}$ cm$^{-3}$ in the pump medium, the already described effect of increased wall relaxation occurs due to the non-polarized rubidium, which settles on the wall.

In contrast, the density of cesium atoms as non-optically pumpable species A2 is 10$^{15}$ cm$^{-3}$. The density of the optically pumpable species A1 (rubidium) is also chosen about a factor 10 smaller, than the one for the non-optically pumpable species A2(cesium). The electron spin relaxation rate $\gamma^{Cs}_{sd}$ of cesium as non-optically pumpable species A2 is situated in the same range, as for rubidium. However, the efficiency of hyperpolarizing $^{129}$Xe for cesium is greater than for rb.

In order to determine the degree of polarization of the electrons of the non-optically pumpable species A2 (equation 2), here the cesium atoms, the effective cross section is determined at about 2*10$^{-14}$ cm$^{-2}$, and as an average value via the relative velocity <σRb-Cε*$^V$>|at 4*10$^{-10}$ cm$^3$s$^{-1}$ at a temperature of 170° C. in the test cell and a relative velocity of rubidium and cesium of 2*10$^4$ cm*s$^{-1}$. The spin exchange rate $\gamma^{Cs,Rb}_{ex}$ between rubidium and cesium is determined by solving equation (3) at 5*10$^5$ s$^{-1}$.

The optical pumping rate R and the spin exchange rate between A1 and A2 must be greater than the electron spin relaxation rates of rubidium and cesium. The exchange rate between cesium and xenon must be greater than the nuclear spin relaxation rate of xenon (y$_w$).

The volume-mediated degree of polarization of the non-optically pumpable species <$P_{cs}$>(z) is therefore 85% following insertion in equation (2).

Since the spin exchange between the alkali atoms rubidium and cesium spin is steady and having a large effective cross section, the spin polarization of the optically pumpable species rubidium may be transferred effectively to the atoms of the non-optically pumpable species cesium, even if the latter is present in a higher density.

In analogy with the equations (2) and (3), the spin exchange rate $\gamma^{Xe,Cs}_{ex}$ and the volume-mediated degree of polarization of $^{129}$Xe may be determined according to equations {5) 25 and (4).

The non-optically pumpable species is chosen in the present case such that the effective cross section $\sigma^{Xe,Cs}$ for the spin transfer to the nucleus of the noble gas atoms is greater than that of the optically pumpable species. The spin exchange rate $\gamma^{Cs,Xe}_{ex}$ between the non-optically pumpable species cesium and nuclei of $^{129}$Xe to be hyperpolarized is according to Equation (5) thus 0.3s$^{-1}$. This value is much greater than the losses due to wall relaxation $\gamma^{Xe}_w$. Thus, about 3 seconds is needed for hyperpolarizing of a xenon atom compared with 50 seconds according to prior art using simple optical pumping. Accordingly, free beam and flow rates may be adjusted in the test cell.

Without limiting the invention, other gas mixture may be hyperpolarized in a test cell. For instance, the following mixtures may be mentioned. The first alkali metal represents the optically pumpable species, the second one, and the non-optically puinpable species in the mixture:

- A $^{85}$Rb-Li(Na, K) mixture for hyperpolarizing $^3$He.
- A K-Li-mixture for hyperpolarizing $^3$He.

Both these mixtures are hyperpolarized in a closed test cell by indirect spin exchange optical pumping without a free beam or bypass flow.

Moreover, with the method according to the invention, besides hyperpolarization of $^{129}$Xe, a $^{85}$Rb-Cs mixture may also be used for hyperpolarization of $^{13}CO_2$. For simple hyperpolarization of $^{13}CO_2$, Rb or Cs isotopes are in principle suitable.

Figure 5:
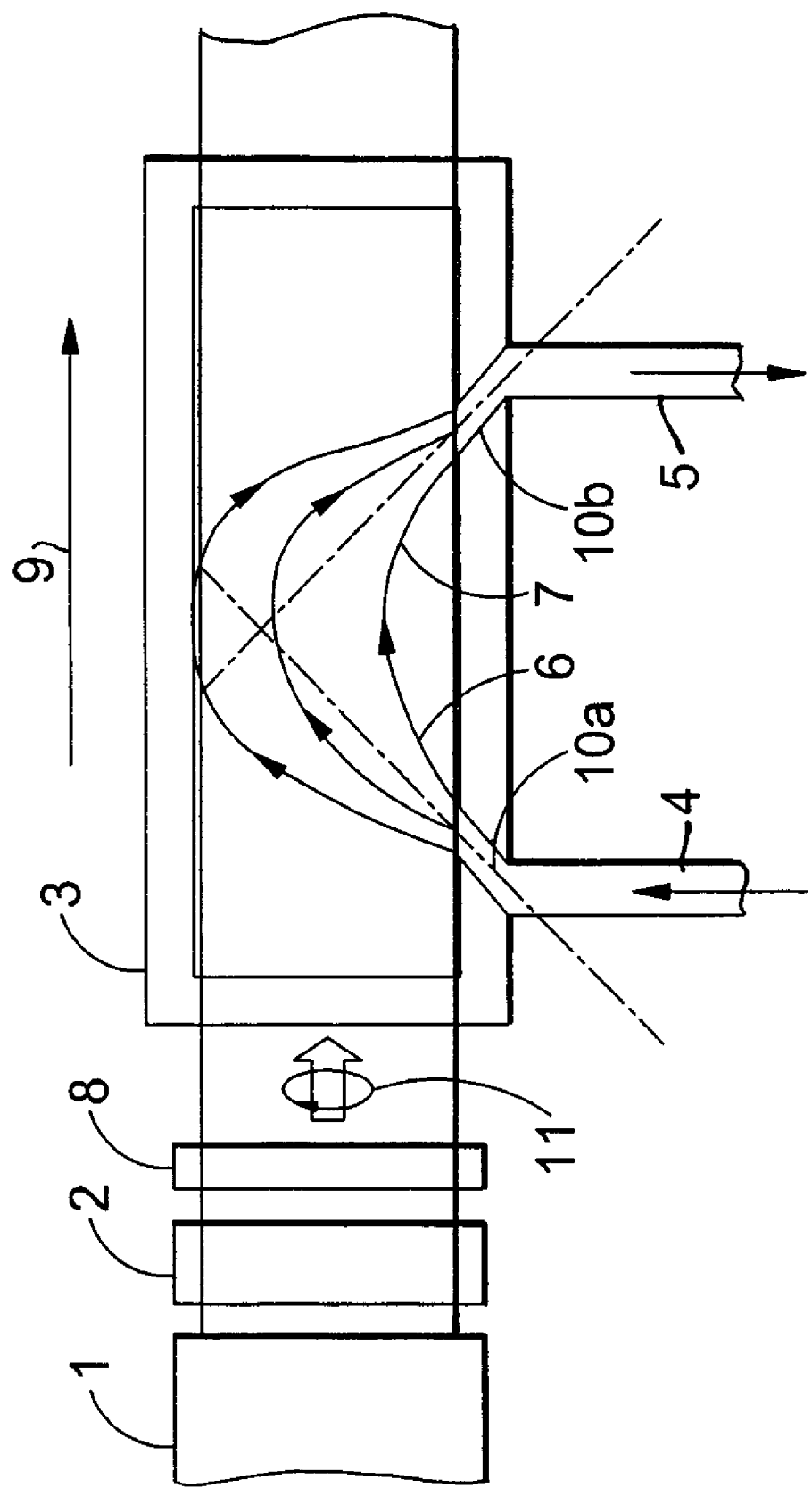

An especially simple design for the optical pump cell with reduced wall relaxation compared with prior art is shown in FIG. 5. It is suited for, e.g., production of hyperpolarized xenon and other noble gases. In contrast to a standard pump cell, the inlet and outlet connections 10a and 10b are inclined at defined angles (6,7) instead of a 90° angle. The objective is to minimize the Rb vapor deposition at the laser inlet window and reduce the interaction of the process-gas flow, as well as contacts with the inner wall of the cell compared to prior art.

A cell with an in- and outlet exhibiting an angle of 45° to the side wall of the cylindrical test cell was realized. The measurements of the absolute Xe polarization shows that with this cell design, Xe polarization in the cell of about 50% may be obtained (about 40 % polarization behind a 7 m long PFA [perfluoralkoxy] hose with an inside diameter of 1.5 mm was measured).

A further increase of the Xe polarization is possible by optimizing the angle of the in- and outlet connection, as well as through radiation of the laser against the direction of flow.

FIG. 5 further shows:
1 Rb laser
2 Polarization optics
3 Test cell
4 Process gas inlet, or inlet for a mixture with atoms to be hyperpolarized
5 Hyperpolarized Xe outlet
6 Median entry angle of the flow into the cell
7 Median exit angle of the flow leaving the cell
8 λ/4 disk for creating circularly polarized lights
9 Magnetic field
10a, 10b In- and outlet connection into the test cell, inclined here about 45° to the longitudinal axis of the test cell.

The invention claimed is:

1. A method for hyperpolarizing atomic nuclei through optical pumping in a optical pumping cell having an inlet and an outlet spaced therefrom, polarization of an electron spin of an optically pumpable species in a mixture created by laser light being transferred to the nuclear spin of an atom to be hyperpolarized, the method comprising the steps of:
feeding components of the mixture through the inlet into the optical pumping cell as a jet flow, drawing the mixture out of the cell through the outlet such that the mixture touches the inner walls of the optical pumping cell only immediately adjacent the outlet, and passing the mixture further on outside the cell for enrichment.

2. The method according to claim 1 wherein the jet flow is inclined in the direction of flow at an acute angle to side wall of the cell when fed into the optical pumping cell.

3. The method according to claim 1, further comprising the step of
feeding a compound for the separation of the mixture from the inner wall into the optical pumping cell.

4. The method according to claim 1 wherein the laser light is radiated into the optical pumping cell perpendicular to the jet flow in the optical pumping cell.

5. The method according to claim 1 wherein the laser light is radiated into the optical pumping cell countercurrent to the jet flow in the optical pumping cell.

6. The method according to claim 1 wherein the mixture is disengaged where the intensity of the laser is largest.

7. The method according to claim 1, further comprising the step of
cooling the walls of the optical pumping cell.

8. The method according to claim 1 wherein the spin exchange is transferred indirectly via a non-optically pumpable species to the nuclear spin of a nucleus to be hyperpolarized.

9. The method according to claim 1 wherein $^{129}$Xe, $^3$He or $^{13}CO_2$ are hyperpolarized.

10. An apparatus for implementing the method according to claim 1, the apparatus comprising:
a cylindrical optical pumping cell having an inlet and an outlet spaced therefrom;
a supply of a mixture of optically pumpable species and hyperpolarizable nuclei connected to the inlet of the cell; and
nozzle means at an inlet of the optical pumping cell for forming and injecting a jet flow of the mixture into the optical pumping cell and for drawing it out through the outlet such that the mixture touches the inner walls of the optical pumping cell only adjacent the outlet and for passing the mixture from the outlet on for enrichment.

11. The apparatus according to claim 10 wherein the inlet or the outlet forms a predetermined acute angle to the longitudinal axis of the optical pumping cell.

12. The apparatus according to claim 10 wherein the means forms a free column for injecting the mixture into the optical pumping cell.

13. The apparatus according to claim 10 wherein the means is a surrounding stream for the mixture.

14. The apparatus according to claim 10 wherein at least one laser is set such that the laser beam is oriented perpendicular and/or countercurrent to the flow of the mixture in the optical pumping cell.

15. The apparatus according to claim 10 wherein the input window or windows of the optical pumping cell have for the laser beam the greatest possible spacing from the input of the optical pumping cell for the optically pumpable species.

16. The apparatus according to claim 10, further comprising:
at least one supply container for a chemical species.

17. The apparatus according claim 10 wherein the supply container is mounted in the supply line(s) of the apparatus.

18. The apparatus according to claim 10, further comprising:
means for cooling walls of the optical pumping cell.

19. The apparatus according to claim 10 wherein the cylindrical cell is centered on an axis, the inlet opening into the cell at the axis and the outlet opening radially into the cell offset from the axis.

* * * * *